United States Patent [19]

Bergersen

[11] Patent Number: 4,986,751
[45] Date of Patent: Jan. 22, 1991

[54] INFANT GUIDANCE PACIFIER APPLIANCE

[76] Inventor: Earl O. Bergersen, 950 Green Bay Rd., Winnetka, Ill. 60093

[21] Appl. No.: 358,436

[22] Filed: May 30, 1989

[51] Int. Cl.$^5$ .............................................. A61C 3/00
[52] U.S. Cl. ...................................................... 433/6
[58] Field of Search .................... 433/6; 128/859, 860, 128/861

[56] References Cited

U.S. PATENT DOCUMENTS

| 4,139,944 | 2/1979 | Bergersen . | |
|---|---|---|---|
| 4,304,227 | 12/1981 | Samelson | 128/861 |
| 4,495,945 | 1/1985 | Liegner | 128/862 |
| 4,580,975 | 4/1986 | Schrems et al. | 433/6 |
| 4,690,640 | 9/1987 | Hinz | 433/6 |
| 4,830,612 | 5/1989 | Bergersen . | |

FOREIGN PATENT DOCUMENTS

| 0293682 | 12/1988 | European Pat. Off. . | |
|---|---|---|---|
| 857129 | 11/1952 | Fed. Rep. of Germany . | |
| 3247074 | 5/1974 | Fed. Rep. of Germany | 433/6 |
| 8603054 | 9/1987 | France . | |

OTHER PUBLICATIONS

Abstract/Zusammenfassung/Abrege 89.120902.5.
Translation of Specification to German Utility Model G 83 15 554.6.

*Primary Examiner*—Cary E. Stone
*Attorney, Agent, or Firm*—Hill, Van Santen, Steadman & Simpson

[57] ABSTRACT

An orthodontic appliance is provided to prevent overbite or overjet from developing in a child. The appliance is U-shaped in plan view and has tooth receiving troughs for the upper and lower teeth to correctly position the jaws antero-posteriorly. Uses of the appliance preferably should begin when the child is in the age range of 12 to 18 months, before all of the deciduous teeth have erupted so that improper development of the jaw can be avoided. The appliance has a non-working portion being a shield and handle portion to cause the appliance to have the appearance of a pacifier as well as to prevent the child from gagging on the appliance and to assist in the proper positioning of the appliance by the child.

13 Claims, 1 Drawing Sheet

INFANT GUIDANCE PACIFIER APPLIANCE

BACKGROUND OF THE INVENTION

1. Field of the Invention

The invention relates to orthodontic positioners and more particularly to a positioner for use in a very young child.

2. Description of the Prior Art

Generally orthodontic treatment is not begun until at least some if not all permanent teeth have erupted, although I have disclosed devices for providing early orthodontic treatment in a mixed dentition stage (U.S. Pat. No. 4,139,944) or in a deciduous dentition stage, such as in my co-pending patent application Ser. No. 054,287. These devices are to be used once the deciduous teeth have all erupted. Generally these devices have not been designed for the very young child, that is less than 3 or 4 years of age and thus initial treatment is delayed until that point.

SUMMARY OF THE INVENTION

The present invention provides an appliance designed for the 1½ year old up to about a 4-6 year old. This appliance is a modification of a pacifier for the young infant to wear prior to starting school. The purpose of the appliance is to properly align the upper and lower jaws antero-posteriorly while the posterior deciduous teeth erupt. As the infant normally would be weaned away from the pacifier, the child is given this mature pacifier which doubles as a pre-treatment appliance to prevent overjet and overbite from developing as the deciduous teeth erupt into place. There is a strong association between jaw relation at a young age (e.g. 2 years of age) and the final overjet and overbite at full maturity (e.g. 18 years of age). This trend of mandibular underdevelopment sets up a relationship at 18 months to 2½ years that is not readily altered afterwards. In other words, when the mandible starts out in a recessive position in relation to the maxilla, it generally stays there, particularly after the deciduous teeth erupt into place (both anterior and posterior). With the jaws in this position, the relationship becomes somewhat permanent and resists antero-posterior positional change with teeth intercuspating posteriorly and particularly with the interiors locked into position via the overbite.

The purpose of this early appliance is to unlock this mandibular recessiveness at a critical time of deciduous tooth eruption. The child wears the appliance as the pacifier was worn at a younger age and the child is not particularly encouraged to stop its wear as one would do with the pacifier. The wear of the appliance can be stopped when the jaw relation is normal or within a relatively small deviation, for example an ⅛", from upper to lower antero-posteriorly in the anterior segment-incisally. The child should be encouraged to wear the appliance at night and as many hours during the day as desired. The device is to be worn passively and will passively guide the jaws and teeth into their proper relation.

The appliance is made of a an inner U-shaped soft plastic upper and lower trough with a horizontal plate of plastic that separates the upper from the lower jaw. The segment of the appliance made up of the two U-shaped troughs separated by a sheet of plastic between the jaws is the working part while a front shield and handle make up a non-working portion which is not a necessary part of the appliance, but helps to make the appliance resemble a pacifier and prevents the child from gagging on the working portion. It also helps the appliance to be positioned properly by the child.

The appliance can be provided in several sizes, from smaller to larger, as the child matures to about 4 to 6 years of age. The smallest size would extend posteriorly only slightly beyond the canines and would be worn from 12 months up to about 20 months. The next size would extend back to about the distal surface of the first deciduous molar and would have slightly higher margins on the labial section of the working U-shaped trough. This appliance would be worn from about 20 to 30 months. The largest size would have a trough that would extend to the distal surface of the second deciduous molars. Its margins on the labial side of the inner working trough would be slightly higher than that of the middle size and the shield could be made slightly smaller. This larger size would be worn from about 30 months of age to final termination about 4 to 6 years of age.

Preferably, the appliance would be completely made of soft plastic in a one-piece construction although various portions, such as the handle, could be separately attached.

DESCRIPTION OF THE PREFERRED EMBODIMENTS

Figure 1:
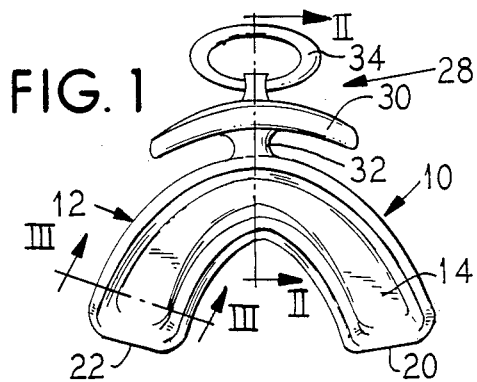
FIG. 1 is an occlusal view of a device embodying the principles of the present invention being a small initial size.
Figure 2:
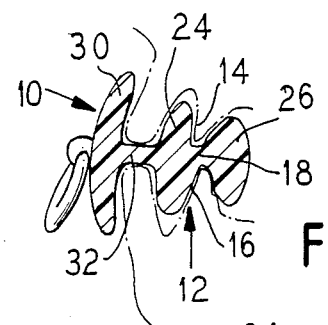
FIG. 2 is a side sectional view of the appliance taken generally along the line II—II of FIG. 1.
Figure 3:
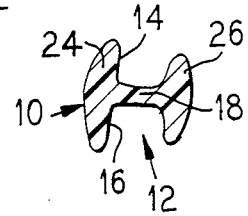
FIG. 3 is a sectional view of the appliance taken generally the line III—III of FIG. 1.

An appliance 10 is illustrated in FIGS. 1-3 which is designed for a very young child, preferably in the age range of about 12 months to 20 months. The appliance has a working portion 12 which is made up of two U-shaped troughs 14, 16 separated by a sheet or web of plastic material 18 such that the troughs open oppositely to receive the upper and lower rows of deciduous teeth of the infant. The troughs extend posteriorly to rear terminal edges 20, 22 which would be positioned only slightly behind the canines of the infant. The U-shaped trough has a labial wall 24 and a lingual wall 26 which, together with the web 18 define the troughs. These troughs, unlike the troughs disclosed in my prior patents and patent applications, are continuous, smooth troughs, and do not include individual tooth receiving pockets or sockets since it is the aim of this appliance to correctly position the patient's jaw, not teeth.

The appliance 10 has a non-working portion 28 which includes a shield 30 which overlies an anterior portion of the infant's lips and is sufficiently large so as to prevent the working portion 12 from dislodging and moving rearwardly in the infant's mouth which might cause gagging. The shield, which is attached to the working portion 12 by a connecting portion 32, also makes the appliance resemble a pacifier which the infant may be accustomed to wearing. This resemblance assists in transitioning from a normal pacifier to this appliance. The shield 30 may also have a handle 34 pivotally connected thereto to provide added assistance for the child in picking up and properly positioning the appliance within the mouth.

Figure 4:
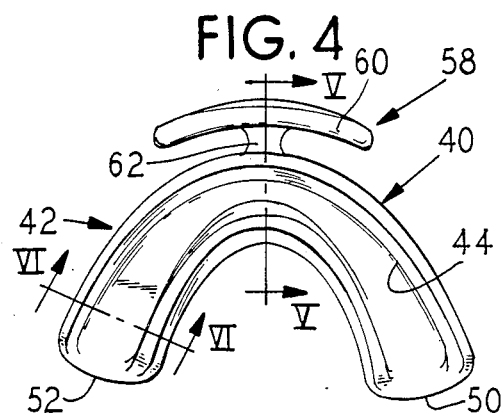
FIG. 4 is an occlusal view of a medium or intermediate size appliance.
Figure 5:
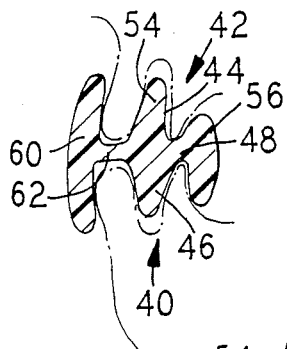
FIG. 5 is a side sectional view taken generally the line V—V of FIG. 4.
Figure 6:
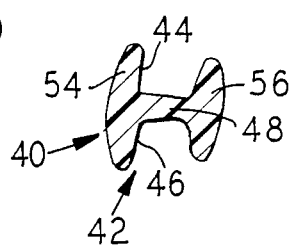
FIG. 6 is a sectional view of the appliance taken generally the line VI—VI of FIG. 4.

FIGS. 4–6 illustrate an appliance 40 which is substantially similar to the appliance illustrated in FIGS. 1–3, but which is of a slightly larger size and which is designed to be worn during an age range of about 20–30 months. Again, the appliance has a working portion 42 made up of two U-shaped troughs 44, 46 separated by a web or sheet 48 of plastic material. The distal ends 50, 52 of the troughs extend back to about the distal surface of the first deciduous molar of the child which should have erupted by this age. The labial wall 54 and lingual wall 56 are slightly higher than the smaller size illustrated in FIGS. 1–3.

Again, there is a non-working portion 58 which comprises a shield 60 secured to the working portion 42 by a connecting member 62. Although a handle is not illustrated in FIGS. 4–6, such a handle could be attached to the shield if desireable.

Figure 7:
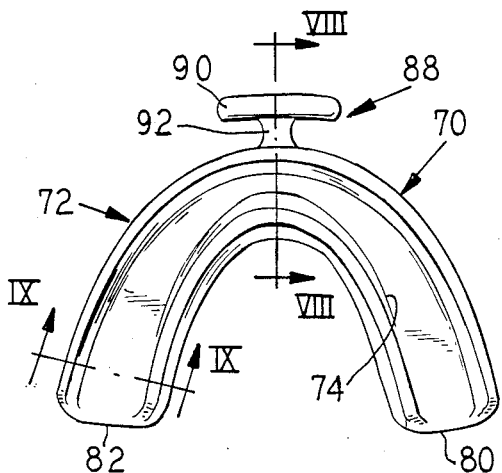
FIG. 7 is an occlusal view of a large sized appliance.
Figure 8:
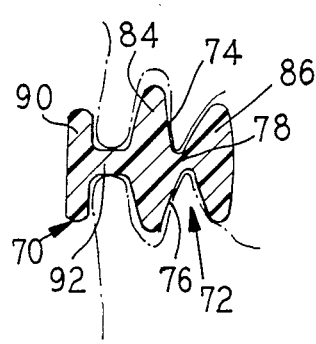
FIG. 8 is a side sectional view taken generally along the line VIII—VIII of FIG. 7.
Figure 9:
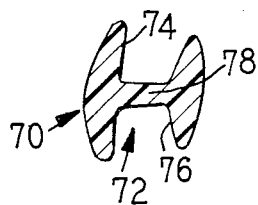
FIG. 9 is a sectional view taken generally along the line IX—IX of FIG. 7.

In FIG. 7–9 a larger appliance 70 is illustrated which again is substantially similar to each of the above described appliances in that it has a working portion 72 comprising two U-shaped troughs 74, 76 separated by a sheet or web 78 of plastic material. Posterior ends 80, 82 of the appliance extend rearwardly to just distally of the second deciduous molars since the appliance is to be worn during the age range of about 30 months to about 4 to 6 years. At this time the second deciduous molars will have erupted.

Again, the troughs are formed by a labial wall 84 and a lingual wall 86, these walls being higher than those present in the middle size appliance 40. A non-working portion 88 of the appliance again includes a shield 90 which can be smaller than the previously described shields in that by this age level the likelihood of the child gagging on the appliance would be substantially reduced and thus the shield, which is attached to the working part 72 by a connecting portion 92, would be useful primarily as a grasping device to assist a child in manipulating the appliance for positioning the appliance in the mouth and removing it. Again, if desireable, a handle could be attached to the shield to further facilitate grasping.

In each of the appliances the upper and lower troughs will be formed in a spacial relationship conforming to the desired antero-posterior relationship of the upper and lower jaws so that as the deciduous teeth erupt mandibular under development is avoided. In this manner, more extensive treatment at later stages may be avoided and certain conditions which are not easily corrected later on can be corrected in a passive manner.

As is apparent from the foregoing specification, the invention is susceptible of being embodied with various alterations and modifications which may differ particularly from those that have been described in the preceding specification and description. It should be understood that I wish to embody within the scope of the patent warranted hereon all such modifications as reasonably and properly come within the scope of my contribution to the art.

I claim as my invention:

1. An orthodontic appliance of the type which is generally U-shaped in plan view and which includes a pair of oppositely directed tooth receiving troughs for the upper and lower rows of a patient's teeth, said troughs being formed between a labial buccal flange and lingual flange and terminating substantially at a distal side of the patient's canine teeth, and further including a manual grasping portion to be exposed on the exterior of the patient's mouth with a connecting portion passing between the patient's lips to secure the grasping portion to the U-shaped portion.

2. An orthodontic appliance according to claim 1, wherein said manual grasping portion comprises a shield for overlying an anterior side of the patient's lips.

3. An orthodontic appliance according to claim 2, wherein said manual grasping member further comprises a handle portion attached to an anterior side of said shield member.

4. An orthodontic appliance according to claim 1, wherein said appliance is to be worn by a child in the age range of about 12 months to 20 months, and said troughs extend rearwardly at least to a distal side of the child's canines.

5. An orthodontic appliance according to claim 1, wherein said troughs are smooth and are without surface deviators.

6. A method of positioning the jaws of a young child comprising the steps:
   providing an orthodontic positioner of the type which is generally U-shaped in plan view and includes a tooth receiving trough in a top and bottom thereof, said providing step comprising selecting a preformed positioner having rear terminal edges extending at least to the distal sides of the erupted deciduous teeth of the child,
   applying the positioner for use by the child at a deciduous dentition stage of development beginning when the child is at an age range of about 12–18 months, before all of the deciduous teeth have erupted, wherein at least some deciduous teeth have erupted, by applying said selected preformed positioner to the child's teeth, such use continuing for at least a portion of the time from the initial application of the positioner to the time that the jaws are properly positioned antero-posteriorly.

7. A method according to claim 6, wherein said providing and applying steps are repeated a plurality of times as additional deciduous teeth erupt so that increasingly larger appliances are provided and applied.

8. A method according to claim 7, wherein each appliance provided and applied has a pair of distal ends which extend distally of the most posterior erupted deciduous teeth.

9. A method of positioning the jaws of a young child comprising the following steps:
   providing an orthodontic positioner of the type which is generally U-shaped in plan view and includes a tooth receiving trough in a top and bottom thereof, said providing step comprising selecting a preformed positioner having rear terminal edges extending at least to the distal sides of the erupted deciduous teeth of the child;
   applying the positioner for use by the child, when the child is at an age range of about 12 to 18 months, and before all of the child's deciduous teeth have erupted, by applying said selected preformed positioner to the child's teeth, such use continuing for at least a portion of the time from the initial application of the positioner to the time that the jaws are properly positioned antero-posteriorly.

10. An orthodontic appliance of the type which is generally U-shaped in plan view and which includes a pair of oppositely directed tooth receiving troughs for the upper and lower rows of a patient's teeth, said troughs being formed between a labial buccal flange and a lingual flange and terminating substantially at a proximal side of the patient's first deciduous molars, and further including a manual grasping portion to be exposed on the exterior of the patient's mouth with a connecting portion passing between the patient's lips to secure the grasping portion to the U-shaped portion.

11. An orthodontic jaw positioning device according to claim 10, wherein said manual grasping portion comprises a shield member for overlying an anterior side of a patient's lips and said connecting portion is positioned on said working portion to extend between the patient's lips.

12. An orthodontic jaw positioning device according to claim 10, wherein said manual grasping portion further comprises a handle portion attached to an anterior side of said shield member.

13. An orthodontic jaw positioning device according to claim 10, wherein said troughs are smooth and are without surface deviations.

* * * * *